(12) United States Patent
Cho

(10) Patent No.: US 12,279,749 B2
(45) Date of Patent: Apr. 22, 2025

(54) DISPOSABLE ENDOSCOPE CANNULA

(71) Applicant: Seunghyuk Cho, Seoul (KR)

(72) Inventor: Seunghyuk Cho, Seoul (KR)

( * ) Notice: Subject to any disclaimer, the term of this patent is extended or adjusted under 35 U.S.C. 154(b) by 590 days.

(21) Appl. No.: 17/612,552

(22) PCT Filed: Apr. 17, 2020

(86) PCT No.: PCT/KR2020/005184
§ 371 (c)(1),
(2) Date: Nov. 18, 2021

(87) PCT Pub. No.: WO2021/015398
PCT Pub. Date: Jan. 28, 2021

(65) Prior Publication Data
US 2022/0304558 A1    Sep. 29, 2022

(30) Foreign Application Priority Data
Jul. 24, 2019 (KR) .................... 10-2019-0089713

(51) Int. Cl.
| | |
|---|---|
| *A61B 1/00* | (2006.01) |
| *A61B 1/015* | (2006.01) |
| *A61B 1/317* | (2006.01) |
| *A61B 17/34* | (2006.01) |

(52) U.S. Cl.
CPC ...... *A61B 1/00103* (2013.01); *A61B 1/00105* (2013.01); *A61B 1/00119* (2013.01); *A61B 1/00135* (2013.01); *A61B 1/015* (2013.01); *A61B 1/317* (2013.01); *A61B 17/34* (2013.01)

(58) Field of Classification Search
CPC ........... A61B 1/00105; A61B 1/00119; A61B 1/00138; A61B 1/015; A61B 1/317; A61B 1/00103; A61B 1/00135
See application file for complete search history.

(56) References Cited

U.S. PATENT DOCUMENTS

| | | | | |
|---|---|---|---|---|
| 4,972,827 A | * | 11/1990 | Kishi | A61B 1/313 600/114 |
| 4,973,321 A | * | 11/1990 | Michelson | A61B 1/317 600/114 |
| 5,695,448 A | * | 12/1997 | Kimura | A61B 1/0005 600/125 |
| 6,086,542 A | * | 7/2000 | Glowa | A61B 5/03 604/27 |
| 8,579,948 B2 | | 11/2013 | Biedermann et al. | |

(Continued)

FOREIGN PATENT DOCUMENTS

| | | |
|---|---|---|
| JP | 2017-023504 A | 2/2017 |
| KR | 10-2009-0113647 A | 11/2009 |

(Continued)

*Primary Examiner* — Aaron B Fairchild
(74) *Attorney, Agent, or Firm* — Rabin & Berdo, P.C.

(57) ABSTRACT

A disposable endoscope cannula which can prevent infection caused by reuse includes an intubation part formed in a predetermined length and insertable into a human body, a binding part connected in the rear of the intubation part and fastened to a trocar part or a scope part to be detachable, and a fluid flow-in and out part mounted on an outer peripheral surface at a front side of the binding part in order to receive or discharge a fluid through the intubation part. The trocar part is fastened to the binding part and inserted through the intubation part.

11 Claims, 4 Drawing Sheets

(56) References Cited

U.S. PATENT DOCUMENTS

| | | | |
|---|---|---|---|
| 9,480,518 B2 | 11/2016 | Biedermann et al. | |
| 2005/0085695 A1* | 4/2005 | Shener ............... | A61B 1/00071 |
| | | | 600/156 |
| 2012/0078038 A1* | 3/2012 | Sahney .............. | A61B 17/3421 |
| | | | 600/104 |

FOREIGN PATENT DOCUMENTS

| | | |
|---|---|---|
| KR | 10-1151310 B1 | 6/2012 |
| KR | 10-2015-0020157 A | 2/2015 |
| KR | 10-2015-0134726 A | 12/2015 |
| KR | 10-1740617 B1 | 5/2017 |
| KR | 101787691 B1 | 10/2017 |

* cited by examiner

DISPOSABLE ENDOSCOPE CANNULA

TECHNICAL FIELD

The present invention relates to a disposable endoscope cannula, and more particularly, to a disposable endoscope cannula which can prevent infection caused by reuse by manufacturing a disposable cannula required for an endoscope for a joint.

BACKGROUND ART

In general, an endoscope is a device inserted into the inside of a subject to see the inside of the human body, and for photographing the inside of the subject or, in some cases, for treating the subject. Since an insertion tube inserted into the inside of the subject for endoscopy is inserted into the inside of the subject, if the tube is contaminated, pathogens may be inserted into the subject, and contaminated by various foreign substances inside the subject.

In particular, in the case of a medical endoscope that uses the human body as the subject, the endoscopic cannula used once is sterilized and reused for other patients, but all parts of a structure may not be sterilized due to a complicated structure of the cannula, so there is a risk that other patients may be secondarily infected. Accordingly, due to the reuse of the contaminated cannula through another patient, there is a problem that the reuse may cause another patient to be inflected due to various diseases and bacteria. For this reason, in order to solve the problem of the contamination of the endoscope, there is a demand for thorough sterilization or a demand for a disposable endoscope cannula that is used only once and discarded.

In the case of prior art, Korean Patent Registration No. 10-1740617 relates to a cannula for minimally invasive surgery, and to a cannula for invasive surgery, and presents technology a structure of a cannula, in which a coupling structure of a sealing member provided in a cannula into which a trocar or surgical tool is inserted is specially configured, so the cannula is designed to ensure that fluids such as blood, air, or water do not flow out to the outside by ensuring that the sealing function is perfectly performed during the operation as well as when the trocar or surgical tool is inserted, so that a surgery operation can be performed safely and conveniently.

The prior art and an endoscope cannula currently used for the surgery are generally reused after sterilization, so the prior art and the endoscope cannula are not thoroughly sterilized, and in particular, foreign substances may remain in a complicated part such as a valve, or the part may be contaminated, and as a result, secondary infection is worrying.

DISCLOSURE

Technical Problem

The present invention is contrived to solve the problem, and has been made in an effort to provide a disposable endoscope cannula which prevents a fear of secondary infection and enabling safe surgery by manufacturing a disposable cannula used for an endoscope.

Technical Solution

In order to achieve the object, the present invention provides a disposable endoscope cannula including: an intubation part formed in a predetermined length and inserted into a human body: a binding part constituted by a detachable tube part connected in the rear of the intubation part and fastened to a trocar part or a scope part to be detachable, and having an insertion seat hole having an open hook so that a projection type light source connection part of the scope part is inserted and seated, and a connection tube part formed in front of the detachable tube part, and having a through-hole so that the fluid which flows out and in through the fluid flow-in and out part is input and discharged, and the intubation part connected to a front side of the through-hole; a fluid flow-in and out part mounted on an outer peripheral surface at a front side of the binding part in order to input or discharge a fluid through the intubation part; and the trocar part fastened to the binding part and inserted through the intubation part.

Further, in order to achieve the object, the present invention provides a disposable endoscope cannula including: an intubation part formed in a predetermined length and inserted into a human body: a binding part constituted by a detachable tube part connected in the rear of the intubation part and fastened to a trocar part or a scope part to be detachable, and constituted by a rotatable mounting hole into which a projection type light source connection part of the scope part is inserted and rotatably mounted, and a connection tube part formed in front of the detachable tube part, and having a through-hole so that the fluid which flows out and in through the fluid flow-in and out part is input and discharged, and the intubation part connected to a front side of the through-hole; a fluid flow-in and out part mounted on an outer peripheral surface at a front side of the binding part in order to input or discharge a fluid through the intubation part; and the trocar part fastened to the binding part and inserted through the intubation part.

In the present invention, the fluid flow-in and out part includes a joint tube expanded so that both the front and rear sides are fixed on the outer peripheral surface of the binding part while the sealing member 34 is inserted into an inner peripheral surface and a center side has a space therein, a flow-in valve part for opening/closing inflow of the fluid, which is connected through the outer peripheral surface of the center side of the joint tube, and a discharge valve part connected to the outer peripheral surface of the center side of the joint tube at an opposite side of the flow-in valve part to open and close the discharge of the fluid.

In the present invention, the trocar part includes a trocar inserted through the intubation part and having the front end portion having a sharp form, a fastening part including a fastening part body fixing the trocar and inserted into the detachable tube part in the rear of the trocar, and a protrusion formed at one side of the fastening part body, and inserted, rotated and coupled into the rotation fastening hole of the detachable tube part, and a handle formed in the rear of the fastening part.

In the present invention, a rotation fastening hole configured by a hole in a form of '┌', which is constituted by a vertical fastening hole into which a protrusion of the trocar part is inserted and a horizontal fastening hole into which the inserted protrusion is rotated and fastened is further formed at an opposite side of the insertion seat hole of the binding part, and a projection part is formed at an inlet side of the horizontal fastening hole, and the protrusion of the trocar part is rotated and seated while passing the projection part.

In the present invention, the rotatable mounting hole is constituted by a vertical mounting hole and a circular mounting hole, and has a form of 'P', and an open hole is formed at the inlet side of the circular mounting hole and the projection type light source connection part of the scope part is inserted and seated.

In the present invention, the binding part and the fluid flow-in and out part are made of a polymer material.

In the present invention, the connection tube part is constituted by a primary connection tube of which diameter is reduced, which is connected to the detachable tube, and a secondary connection tube reduced and connected again in the primary connection tube, and a pair of sealing member seating grooves seated with a sealing member 34 and spaced apart from each other by a predetermined distance, a through-hole forming groove formed between a pair of sealing member seating grooves, and having the through-hole in which the fluid flows in and out through the fluid flow-in and out part, and a joint tube seating groove so that the joint tube is inserted and fixed into the front of the front-side sealing member seating groove through the secondary connection tube are formed on the outer peripheral surface of the secondary connection tube, and a front end portion of the joint tube seating groove is formed as a hook type end portion so that the joint tube may be easily inserted.

Advantageous Effect

According to the present invention, since the disposal endoscope cannula is used for one-time use, the disposal endoscope cannula has an advantage that there is no concern about infection due to reuse.

Further, according to the present invention, since some components of the disposal endoscope cannula are made of a polymer material, the disposal endoscope cannula has an effect that cost by one-time use can be reduced.

Further, according to the present invention, since the disposable endoscope cannula is easily detachable from a scope part, the disposable endoscope cannula has an advantage in use convenience.

BEST MODE

As a best mode for carrying out the present invention, a disposable endoscope cannula includes: an intubation part formed in a predetermined length and inserted into a human body: a binding part constituted by a detachable tube part connected in the rear of the intubation part and fastened to a trocar part or a scope part to be detachable, and having an insertion seat hole having an open hook so that a projection type light source connection part of the scope part is inserted and seated, and a connection tube part formed in front of the detachable tube part, and having a through-hole so that the fluid which flows out and in through the fluid flow-in and out part is input and discharged, and the intubation part connected to a front side of the through-hole; a fluid flow-in and out part mounted on an outer peripheral surface at a front side of the binding part in order to receive or discharge a fluid through the intubation part; and the trocar part fastened to the binding part and inserted through the intubation part.

Mode for Invention

Hereinafter, preferred embodiments of the present invention will be described in detail with reference to the accompanying drawings. However, the embodiments is intended to be described in detail to enable those skilled in the art to easily carry out the invention and it is not meant that the technical spirit and scope of the present invention are limited thereto.

Figure 1:
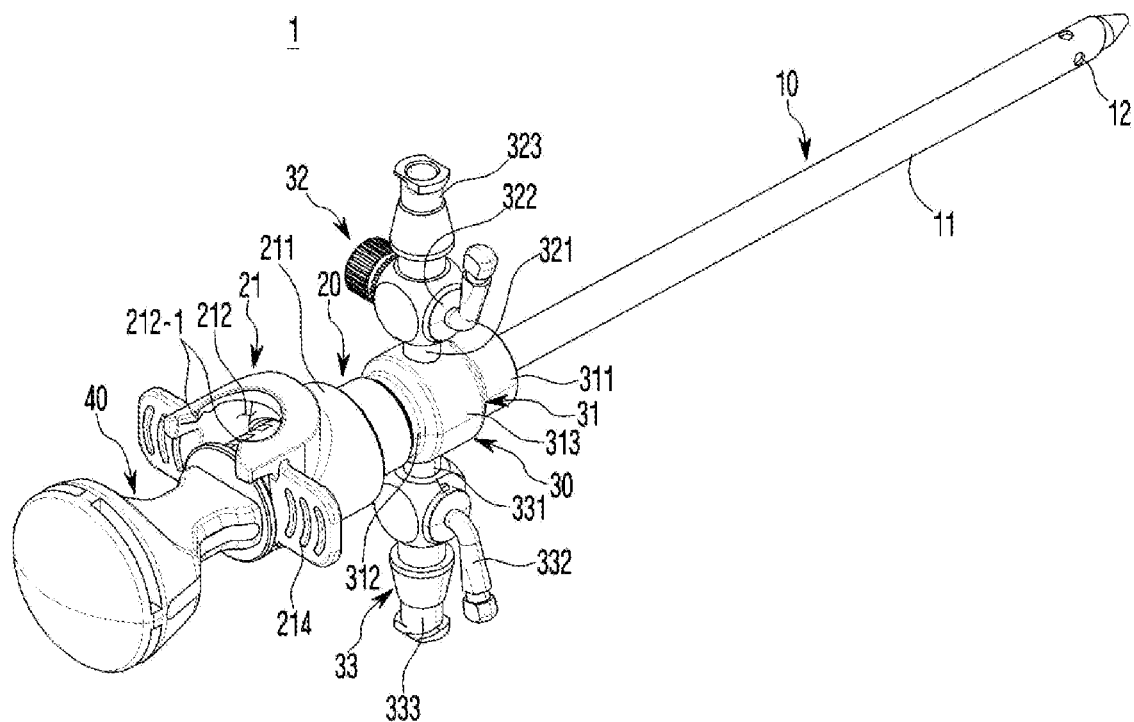
FIG. 1 is a perspective view of a disposable endoscope cannula according to the present invention.
Figure 2:
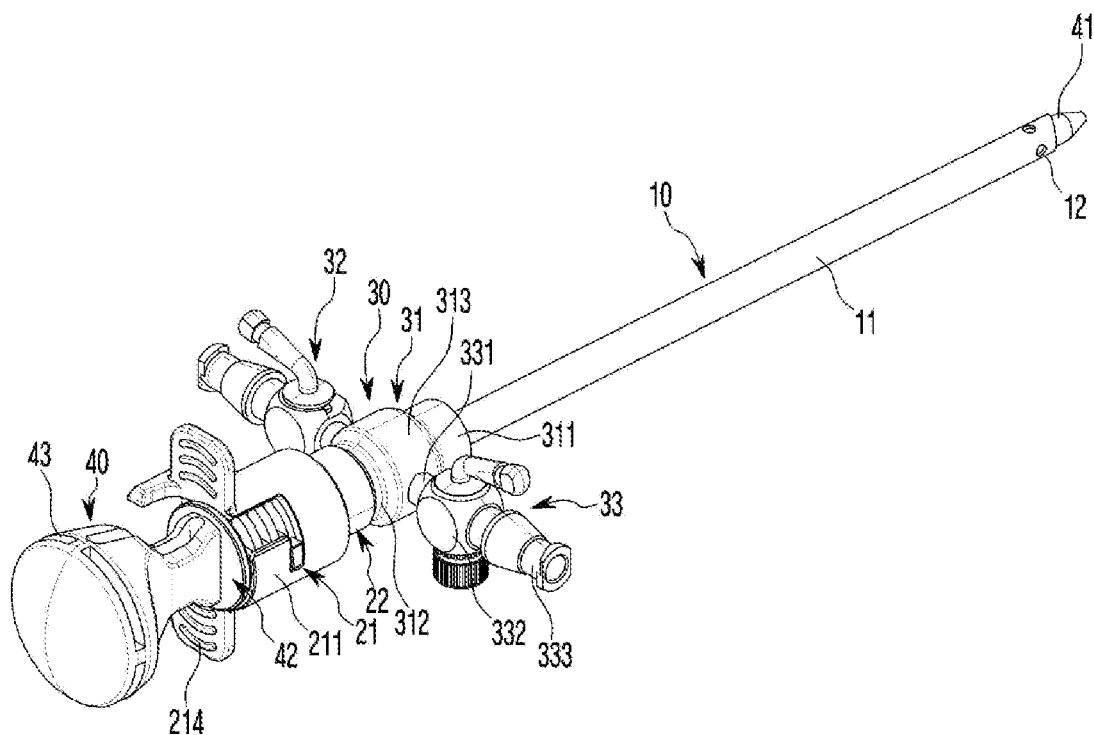
FIG. 2 is a perspective view of the disposable endoscope cannula viewed at another angle according to the present invention.
Figure 3:
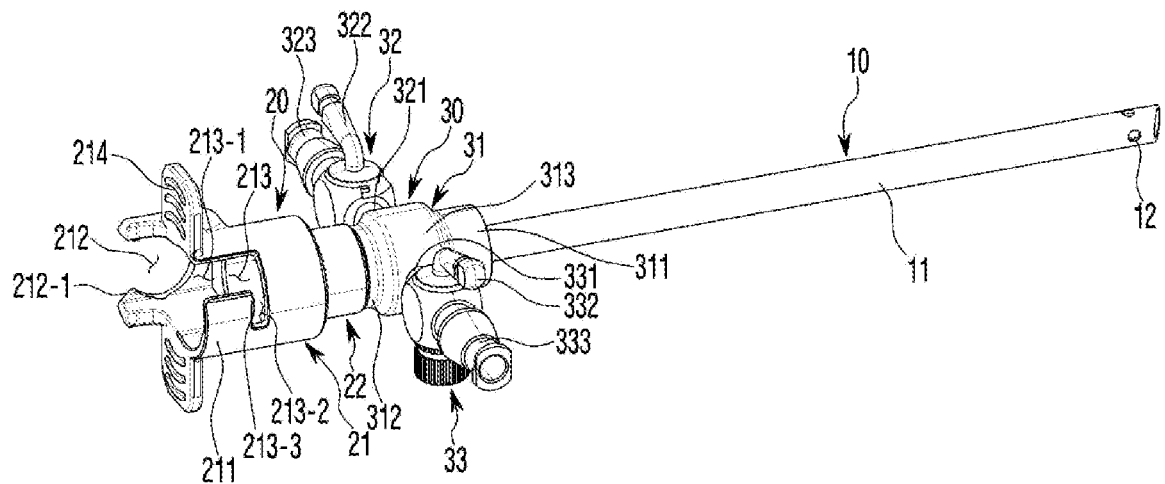
FIG. 3 is a perspective view of a disposable endoscope cannula except for a trocar according to the present invention.
Figure 4:
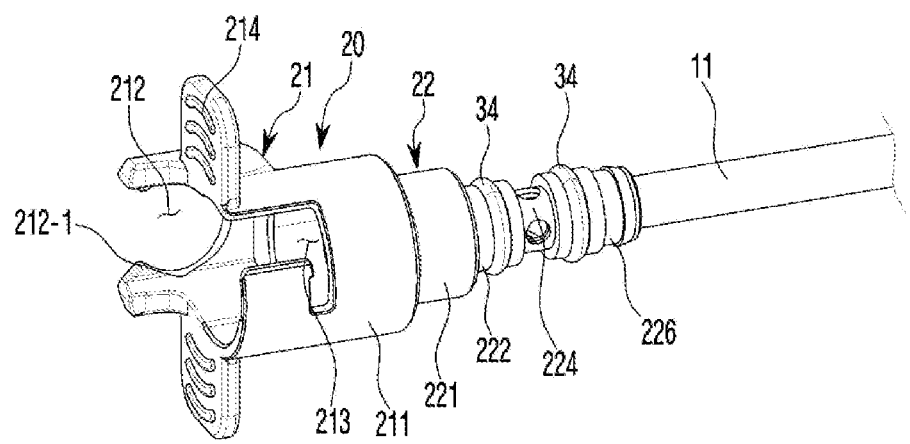
FIG. 4 is a partially enlarged perspective view of the disposable endoscope cannula according to the present invention.
Figure 5:
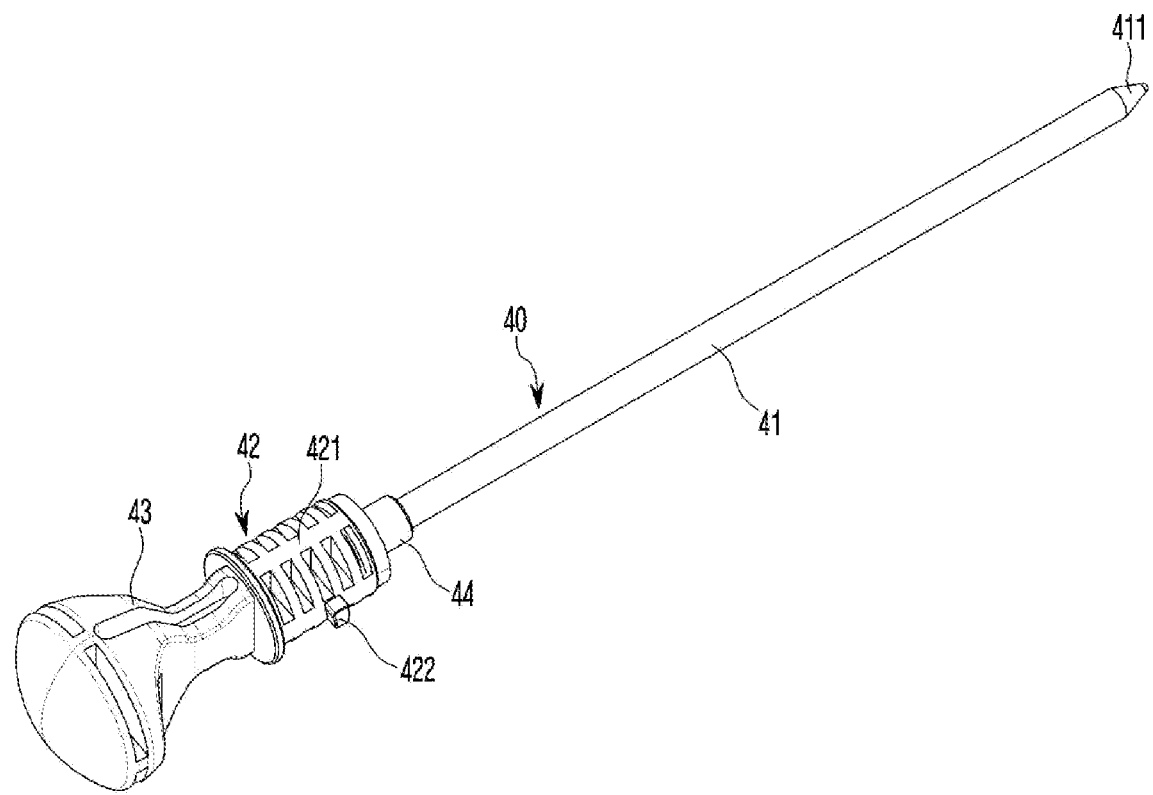
FIG. 5 is a perspective view of the trocar of the disposable endoscope cannula according to the present invention.
Figure 6:
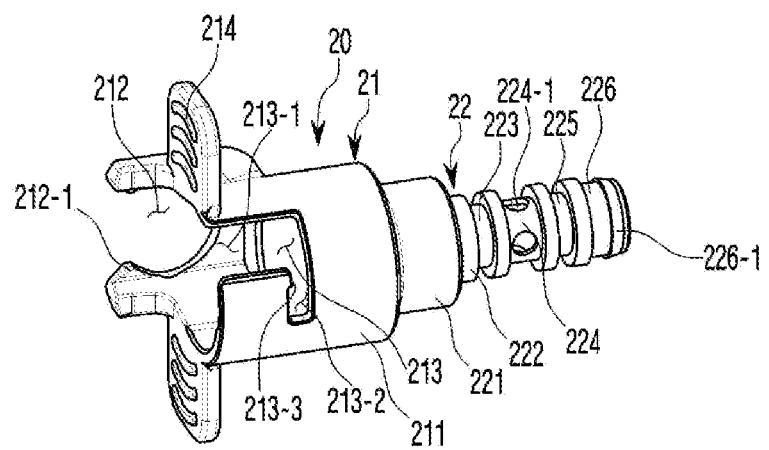
FIG. 6 is a perspective view of a binding part of the disposable endoscope cannula according to the present invention.
Figure 7:
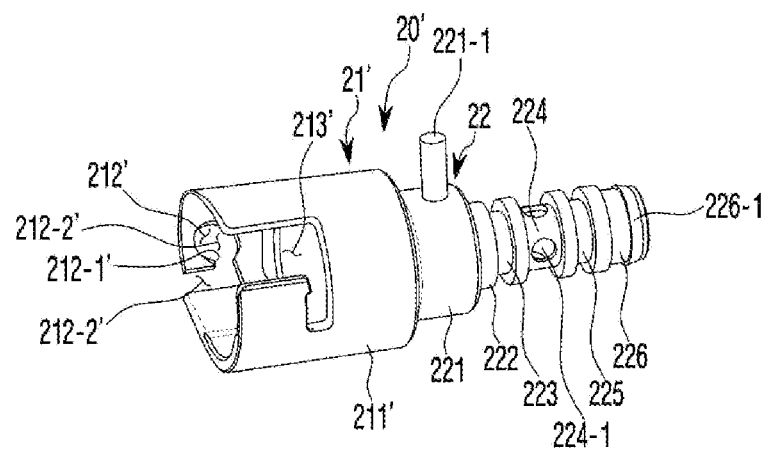
FIG. 7 is a perspective view of another embodiment of the binding part of the disposable endoscope cannula according to the present invention.
Figure 8:
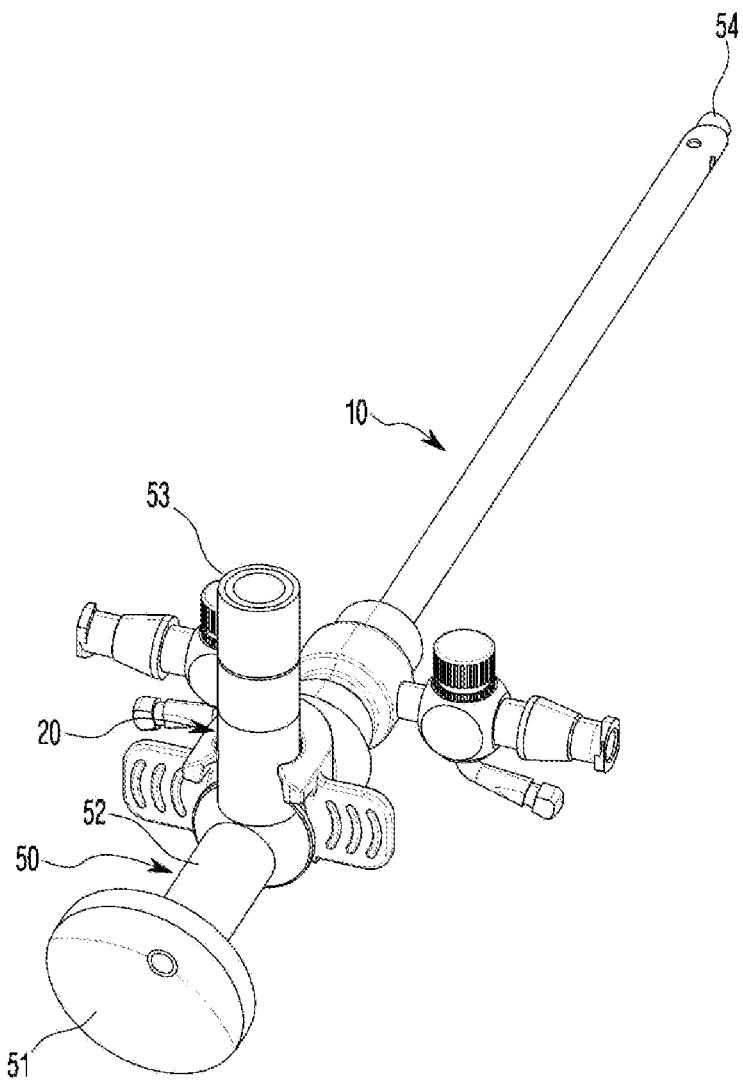
FIG. 8 is a perspective view of a disposable endoscope cannula mounted with a scope part according to the present invention.

FIG. 1 is a perspective view of a disposable endoscope cannula according to the present invention, FIG. 2 is a perspective view of the disposable endoscope cannula viewed at another angle according to the present invention, FIG. 3 is a perspective view of a disposable endoscope cannula except for a trocar according to the present invention, FIG. 4 is a partially enlarged perspective view of the disposable endoscope cannula according to the present invention, FIG. 5 is a perspective view of the trocar of the disposable endoscope cannula according to the present invention, FIG. 6 is a perspective view of a binding part of the disposable endoscope cannula according to the present invention, FIG. 7 is a perspective view of another embodiment of the binding part of the disposable endoscope cannula according to the present invention, and FIG. 8 is a perspective view of a disposable endoscope cannula mounted with a scope part according to the present invention.

The disposal endoscope cannula 1 according to the present invention will be described with reference to FIGS. 1 to 6.

FIG. 1 is a perspective view of a disposable endoscope cannula 1 according to the present invention. As illustrated in the figure, the disposable endoscope cannula 1 is constituted by an intubation part 10 formed in a predetermined length and inserted into a human body: a binding part 20 connected in the rear of the intubation part 10 and fastened to a trocar part 40 or a scope part 50 to be detachable; a fluid flow-in and out part 30 mounted on an outer peripheral surface at a front side of the binding part 20 in order to receive or discharge a fluid through the intubation part 10; and the trocar part 40 fastened to the binding part 20 and inserted through the intubation part 10.

As illustrated in the figure, the intubation part 10 is constituted by an insertion tube inserted into the side of the human body and a fluid flow-in and output hole 12 penetrated on the outer peripheral surface of a front end portion of the insertion tube. Sterilization distilled water which is a fluid supplied through the fluid flow-in and out part 30 is discharged through the fluid flow-in and output hole 12 and the front of the insertion tube, and sucked through the fluid flow-in and output hole 12 and the front of the insertion tube and discharged to the outside.

As illustrated in FIGS. 1 and 2, the binding part 20 is constituted by a detachable tube part 21 constituted by a rotation fastening hole 213 into which a projection 422 of the trocar part 40 is inserted, and rotatably coupled at one side and an insertion seat hole 212 having an open hook 212-1 at one side so that a projection type light source connection part 53 of the scope part 50 is inserted and seated at the other side, and a connection tube part 22 formed in front of the detachable tube part 21, and having a through-hole 224 so that the fluid which flows out and in through the fluid flow-in and out part 30 is input and discharged, and the intubation part 10 connected to a front side of the through-hole 224. The through-hole 224 is radially formed in the intubation tube 11 as illustrated in FIG. 4.

As illustrated in FIGS. 2 to 4, the detachable tube part 21 includes a detachable tube 211, a handle holder 214 formed at a rear end portion of the detachable tube 211 and serving to hold the cannula 1 inserted into the inside of the human body, and an insertion seat hole 212 into which the projection type light source connection part of the scope part 50 is inserted and seated and a rotation fastening hole 213 into which the protrusion 422 formed at the fastening part of the trocar part is rotated, inserted, and seated, which are formed at both sides of the handle holder 214. One side of the insertion seat hole 212 is opened and the open hook 212-1 is formed at one opened side to serve to fix the projection type light source connection part 53 not to be easily released after the inserted projection type light source connection part 53 is inserted. The open hook 212-1 may be formed at any one side of the opened part or formed at both sides. The opened part of the open hook 212-1 is also formed to be smaller than a diameter of the projection type light source connection part 53, and as a result, a role of the open hook may be achieved.

As illustrated in FIG. 6, the rotation fastening hole 213 is constituted by a vertical fastening hole 213-1 and a horizontal fastening hole 213-2 connected on an upper end of the vertical fastening hole 213-1, and overall is formed in a form of 'r'. The projection part 213-2 may be formed at an inlet side of the horizontal fastening hole 213-2, and the protrusion 422 of the trocar part 40 may be rotated and seated while passing through the projection part 213-3. The projection part 213-3 serves to fix the protrusion 422 so as not to be easily released.

As illustrated in FIG. 6, the connection tube part 22 is formed integrally with the detachable tube part 21, and constituted by a primary connection tube 221 sequentially reduced so that the trocar 41 or a scope body 54 connected to the detachable tube part 21 and inserted into the detachable tube 211 may be easily inserted, and a secondary connection tube 222 which is reduced and connected in the primary connection tube 222 again. A pair of sealing member seating grooves 223 and 225 seated with a sealing member 34 and spaced apart from each other by a predetermined distance, a through-hole forming groove 224 formed between a pair of sealing member seating grooves 223 and 225, and having the through-hole 224-1 in which the fluid flows in and out through the fluid flow-in and out part 30, and a joint tube seating groove 225 so that the joint tube 31 is inserted and fixed into the front of the front-side sealing member seating groove 225 through the secondary connection tube 222 are formed on the outer peripheral surface of the secondary connection tube 222. A front end portion of the joint tube seating groove 226 is formed as a hook type end portion 226-1 so that the joint tube 31 may be easily inserted.

Next, as illustrated in FIGS. 1 to 3, the fluid flow-in and out part 30 will be described. The fluid flow-in and out part 30 is constituted by a joint tube 31 expanded so that a front side 311 and a rear side 312 are fixed on the outer peripheral surface of the binding part 20 while the sealing member 34 is inserted into an inner peripheral surface and a center side 313 has a space therein, a flow-in valve part 32 for opening/closing inflow of the fluid, which is connected through the outer peripheral surface of the center side of the joint tube 31, and a discharge valve part 33 connected to an opposite side of the flow-in valve part 32 through the outer peripheral surface of the center side 313 of the joint tube 31 to open and close the discharge of the fluid. As illustrated in FIG. 4, the joint tube 31 inserted through the secondary connection tube is sealed and fixed by the sealing member 34 seated on a pair of sealing member seating grooves 223 and 225, and a hook type protrusion (not illustrated) is radially formed on the inner peripheral surface of the front-side joint tube 31 so as to be fixed to the joint tube seating groove 226 and inserted through the hook type end portion 226-1 formed in front of the joint tube seating groove 226, and the hook type protrusion is suspended on the hook type end portion 226-1 to fix the location of the joint tube 31. As a result, a space capable of temporarily storing the fluid is provided in the expanded center-side joint tube 313, and sterilization distilled water which is the fluid may easily flow in and out to the human body through the insertion tube 11 through the space. The flow-in valve part 32 is constituted by a nipple 321 connected to the center side 313 of the joint tube 31, a valve 322 connected to the nipple 321, and a flow-in tube 323 connected to the valve 322 and connected to a fluid supply line (not illustrated). The discharge valve part 32 is also formed in the same form, and the discharge valve part 33 is constituted by a nipple 331 connected to the center side 313 of the joint tube 31, a valve 332 connected to the nipple 331, and a flow-out tube 333 connected to the valve 332 and connected to a fluid supply line (not illustrated).

Next, the trocar part 40 illustrated in FIG. 5 is constituted by a trocar inserted through the intubation part 10 and having the front end portion 411 having a sharp form, a fastening part 42 including a fastening part body 421 fixing the trocar 41 and inserted into the detachable tube part 21 in the rear of the trocar 41, and a protrusion 422 formed at one side of the fastening part body 421, and inserted, rotated and coupled into the rotation fastening hole 213 of the detachable tube part 21, and a handle 43 formed in the rear of the fastening part 42. The trocar 41 is inserted into the inside of the intubation 10 and input into the human body while the trocar 41 is inserted. In addition, the trocar part 40 is removed and the scope body 54 is inserted into the insertion tube 11. Accordingly, the front end 411 of the trocar 41 is formed to be sharp to be easily inserted into the inside of the human body. The trocar 41 is connected to the fastening part 42 through the trocar connection part 44. The fastening part 42 may have a diameter smaller than the diameter of the detachable tube 211, and multiple grooves may be formed in the fastening part 42 in order to reduce a weight. The protrusion 422 is formed in the fastening part 42 to be inserted into the rotation fastening hole 213 to be rotated and fastened, and the protrusion 422 is passed and seated while rotating the projection part 213-3 of the rotation fastening hole 213. The protrusion 422 may be easily released from the rotation fastening hole 213, but fixed by the projection part 213-3. The handle 43 is formed in the rear of the fastening part 42, and the intubation part 10 and the trocar part 40 may be inserted into the human body or the trocar part 40 may be extracted to the outside by using the handle 43.

FIG. 7 illustrates another embodiment of a binding part 20' according to the present invention. The binding part 20' is constituted by a detachable tube part 21' constituted by a rotation fastening hole 213' into which a projection 422 of the trocar part 40 is inserted, and rotatably coupled at one side and an insertion seat hole 212 having an open hook 212-1 at one side so that a projection type light source connection part 53 of the scope part is inserted and rotatably mounted at the other side, and a connection tube part 22 formed in front of the detachable tube part 21', and having a through-hole 224-1 so that the fluid which flows out and in through the fluid flow-in and out part 30 is input and discharged, and the intubation part 10 connected to a front side of the through-hole 224-1. The binding part 20' is different from the binding part 20 of an embodiment in a scheme in which the projection type light source connection part 53 of the scope part is connected. In the scheme in which the projection type light source connection part 53 of the scope part 50 is connected, the projection type light source connection part 53 is first inserted and rotated, and then the projection type light source connection part 53 is finally seated. That is, the rotatable mounting hole 212' is constituted by a vertical mounting hole 212-1' of which one side is opened so as to insert the projection type light source connection part 53 and a circular mounting hole 212-2' formed in a horizontal direction on an end portion of the vertical mounting hole 212-1'. An open hook 212-3' is formed at an inlet side of the circular mounting hole 212-2' to prevent the projection type light source connection part 53 from being easily released after insertion.

The connection tube part 22 of FIG. 7 is formed integrally with the detachable tube part 21', and constituted by a primary connection tube 221 sequentially reduced from the detachable tube 211' so that the trocar 41 or a scope body 54 connected to the detachable tube part 21' and inserted into the detachable tube 211' may be easily inserted, and a secondary connection tube 222 which is reduced and connected in the primary connection tube 222 again. A pair of sealing member seating grooves 223 and 225 on which the sealing member 34 is seated and the through-hole forming groove 224 with the through-hole 224-1 in which the fluid which flows in and out through the fluid flow-in and out part 30 are formed between a pair of sealing member seating grooves 223 and 225 on the outer peripheral surface of the secondary connection tube 222. The joint tube seating groove 226 into which the joint tube 31 is inserted and fixed through the secondary connection tube 222 is formed in front of the front-side sealing member seating rove 225. A front end portion of the joint tube seating groove 226 is formed as a hook type end portion 226-1 of which a diameter increases to a rear side so that the joint tube 31 may be easily inserted. The joint tube 31 is inserted through the hook type end portion 226-1 and seated on the joint tube seating groove 226. Further, the inner peripheral surface of the joint tube 31 is sealed by the sealing member 34 seated on the sealing member seating grooves 223 and 225 to prevent the internal fluid from flowing to the outside. The joint tube 31 inserted through the secondary connection tube is sealed and fixed by the sealing member 34 seated on a pair of sealing member seating grooves 223 and 225, and a hook type protrusion (not illustrated) is radially formed on the inner peripheral surface of the front-side joint tube 31 so as to be fixed to the joint tube seating groove 226 and inserted through the hook type end portion 226-1 formed in front of the joint tube seating groove 226, and the hook type protrusion is suspended on the hook type end portion 226-1 to fix the location of the joint tube 31. Further, as illustrated in FIG. 7, a rotatable mounting holder 2211 is formed at one side of the outer peripheral surface of the primary connection tube 221 and the rotatable mounting holder 221-1 is a component which substitutes for the handle holder 214. That is, the trocar part 40 or the scope part 50 is rotated by gripping the rotatable mounting holder 221-1 or the rotatable mounting holder 221-1 is rotated to rotatably fix the trocar part 40 or the scope part 50.

FIG. 8 illustrates a state in which the scope part 50 is fastened to the binding part 20 according to an embodiment. The scope part 50 is constituted by a camera connection part 51 to which an endoscope camera capable of viewing the inside of the human body is connected, a connection tube 52 formed integrally with the camera connection part 51, the projection type light source connection part 53 for connecting a light source to the connection part 52, and the scope body 54 connected to the front of the connection tube 52. As illustrated in the figure, the projection type light source connection part 53 is inserted and seated into the insertion seating hole 212 and the open hook 212-1 is formed at the inlet side of the insertion seating hole 212 to prevent the projection type light source connection part 53 from being easily released. The scope body 54 is inserted into the inside of the human body through the insertion tube 11 and the inside of the human body may be viewed through an endoscope camera (not illustrated) connected to the scope part 50 in real time, and it is also possible to photograph the inside of the human body.

The disposal endoscope cannula 1 according to the present invention is not reused, but removed after being used. Since the disposal endoscope cannula 1 is made of the polymer material, the disposal endoscope cannula 1 may be used more inexpensively than a metallic cannula in terms of cost. However, since the insertion tube 11 and the trocar 41 should maintain durability suitable for a use purpose, it is general that the insertion tube 11 and the trocar 41 are made of metal.

Although the embodiment is described exemplarily, it is apparent to those skilled in the art that the present invention can be embodied in different forms without departing from the intent and scope. Accordingly, it should be regarded that the above-described embodiment is not limited, but exemplary, and the appended claims and all embodiments within a range equivalent thereto will be included in the scope of the present invention.

INDUSTRIAL APPLICABILITY

The present invention relates to a disposable endoscope cannula which can prevent infection caused by reuse by manufacturing a disposable cannula required for an endoscope for a joint, and is an invention which has a highest industrial applicability.

The invention claimed is:
1. A disposable endoscope cannula comprising:
   an intubation part formed in a predetermined length and configured to be insertable into a human body;
   a binding part including
      a detachable tube part, and
      a connection tube part formed in front of the detachable tube part and connected to a rear of the intubation part;

a fluid flow hub mounted on an outer peripheral surface of the binding part at a front side of the binding part, the fluid flow hub being configured to receive or discharge a fluid through the intubation part; and a trocar part fastened to the binding part and inserted through the intubation part;

wherein the detachable tube part is configured to be detachably fastened to the trocar part or a scope part and includes an insertion seat hole having an open hook configured for inserting and seating a light source connection part of the scope part, the connection tube part has a through-hole configured to have the fluid input and discharged therethrough, the intubation part is connected to a front side of the through-hole, and the fluid flow hub includes a joint tube including front and rear sides fixed on the outer peripheral surface of the binding part, a sealing member inserted into an inner peripheral surface of the binding part, and a center side having a space therein, a flow-in valve part for opening and closing to respectively start and stop inflow of the fluid, the flow-in valve part being connected through an outer peripheral surface of the center side of the joint tube, and a discharge valve part connected to the outer peripheral surface of the center side of the joint tube at an opposite side of the flow-in valve part to open and close to respectively start and stop discharge of the fluid.

2. The disposable endoscope cannula of claim 1, wherein the trocar part includes a trocar inserted through the intubation part and having a front end portion having a sharp form, a fastening part including a fastening part body fixing the trocar and inserted into the detachable tube part in a rear of the trocar, and a protrusion formed at one side of the fastening part body, and inserted, rotated and coupled into a rotation fastening hole of the detachable tube part, and a handle formed in a rear of the fastening part.

3. The disposable endoscope cannula of claim 1, wherein a rotation fastening hole configured by a hole in a form of 'ㄱ', which the rotation fastening hole being constituted by a vertical fastening hole into which a protrusion of the trocar part is inserted and a horizontal fastening hole into which the inserted protrusion is rotated and fastened is further formed at an opposite side of the insertion seat hole of the binding part, and a projection part is formed at an inlet side of the horizontal fastening hole, and the protrusion of the trocar part is rotated and seated while passing the projection part.

4. The disposable endoscope cannula of claim 1, wherein the binding part and the fluid flow hub are made of a polymer material.

5. The disposable endoscope cannula of claim 1, wherein the connection tube part by comprises:

a primary connection tube to the detachable tube, and a secondary connection tube connected to the primary connection tube, a pair of sealing member seating grooves seated with a sealing member and spaced apart from each other by a predetermined distance, a through-hole forming groove formed between the pair of sealing member seating grooves, and having the through-hole, and a joint tube seating groove configured so that a joint tube is inserted and fixed into a front of a front-side sealing member seating groove through the secondary connection tube, and wherein the joint tube seating groove and the front-side sealing member seating groove are formed on an outer peripheral surface of the secondary connection tube, and a front end portion of the joint tube seating groove is formed as a hook end portion.

6. A disposable endoscope cannula comprising:

an intubation part formed in a predetermined length and inserted configured to be insertable into a human body;

a binding part including a detachable tube part, and a connection tube part formed in front of the detachable tube part and connected to a rear of the intubation part;

a fluid flow hub mounted on an outer peripheral surface of the binding part at a front side of the binding part, the fluid flow hub being configured to receive or discharge a fluid through the intubation part; and a trocar part fastened to the binding part and inserted through the intubation part;

wherein the detachable tube part is configured to be detachably fastened to the trocar part or a scope part and includes a rotatable mounting hole configured to have a light source connection part of the scope part is inserted and rotatably mounted therein, the connection tube part has a through-hole configured to have the fluid input and discharged therethrough, and the intubation part is connected to a front side of the through-hole, and the fluid flow hub includes a joint tube including front and rear sides fixed on the outer peripheral surface of the binding part, a sealing member inserted into an inner peripheral surface of the binding part, and a center side having a space therein, a flow-in valve part for opening and closing to respectively start and stop inflow of the fluid, the flow-in valve part being connected through an outer peripheral surface of the center side of the joint tube, and a discharge valve part connected to the outer peripheral surface of the center side of the joint tube at an opposite side of the flow-in valve part to open and close to respectively start and stop discharge of the fluid.

7. The disposable endoscope cannula of claim 6, wherein the rotatable mounting hole is constituted by a vertical mounting hole for insertion of the light source connection part of the scope part, and a circular mounting hole for insertion of the light source connection part while rotating the light source connection part, and the rotatable mounting hole has a form of 'P', and an open hook is formed at an inlet side of the circular mounting hole.

8. The disposable endoscope cannula of claim 6, wherein the trocar part includes a trocar inserted through the intubation part and having a front end portion having a sharp form, a fastening part including a fastening part body fixing the trocar and inserted into the detachable tube part in a rear of the trocar, and a protrusion formed at one side of the fastening part body, and inserted, rotated and coupled into a rotation fastening hole of the detachable tube part, and a handle formed in a rear of the fastening part.

9. The disposable endoscope cannula of claim 6, wherein a rotation fastening hole configured by a hole in a form of 'Γ', the rotation fastening hole being constituted by a vertical fastening hole into which a protrusion of the trocar part is inserted and a horizontal fastening hole into which the inserted protrusion is rotated and fastened is further formed at an opposite side of the insertion seat hole of the binding part, and a projection part is formed at an inlet side of the horizontal fastening hole, and the protrusion of the trocar part is rotated and seated while passing the projection part.

10. The disposable endoscope cannula of claim 6, wherein the binding part and the fluid flow hub are made of a polymer material.

11. The disposable endoscope cannula of claim 6, wherein the connection tube part comprises:

a primary connection tube connected to the detachable tube, and a secondary connection tube connected to the primary connection tube, a pair of sealing member seating grooves seated with a sealing member and spaced apart from each other by a predetermined distance, a through-hole forming groove formed between the pair of sealing member seating grooves, and having the through-hole, and a joint tube seating groove configured so that a joint tube is inserted and fixed into a front of a front-side sealing member seating groove through the secondary connection tube, and wherein the joint tube seating groove and the front-side sealing member seating groove are formed on an outer peripheral surface of the secondary connection tube, and a front end portion of the joint tube seating groove is formed as a hook end portion.

\* \* \* \* \*